United States Patent [19]

Mirejovsky et al.

[11] Patent Number: 4,743,588

[45] Date of Patent: May 10, 1988

[54] COMPOSITIONS AND METHODS OF ENHANCING TRANSDERMAL AND TRANSMEMBRANE PENETRATION SYSTEMIC AGENTS

[75] Inventors: Dorla Mirejovsky, Irvine; Harun Takruri, Laguna Niguel, both of Calif.

[73] Assignee: Allergan Pharmaceuticals, Inc., Irvine, Calif.

[21] Appl. No.: 620,229

[22] Filed: Jun. 13, 1984

[51] Int. Cl.⁴ .................... A61K 31/70; A61K 31/56; A61K 31/16
[52] U.S. Cl. ........................................ 514/24; 514/29; 514/169; 514/625; 514/629; 514/947
[58] Field of Search ................. 514/169, 178, 179, 24, 514/29, 625, 629, 947

[56] References Cited

PUBLICATIONS

Chemical Abstracts; vol. 82 (1975); #39533u; McGovern et al.
Chemical Abstracts; vol. 83 (1975); #1758d; Fisch et al.
Franz, "Journal of Investigative Derm. (1975) 64 pp. 190, 195.
Chem. Abstracts vol. 95 (1981) Par. 145285t.

*Primary Examiner*—Leonard Schenkman
*Assistant Examiner*—Joseph A. Lipovsky
*Attorney, Agent, or Firm*—Joseph A. Marlino; Stuart R. Suter; Alan D. Lourie

[57] ABSTRACT

Compositions and methods useful for enhancing the transdermal and transmembrane drug delivery of topical and systemic agents. The compositions and methods comprise the active agent together with an effective amount of certain amides of heterocyclic amines as defined herein as penetration enhancers and topically administering to human or animal skin or other membranes the resulting compositions.

12 Claims, No Drawings

COMPOSITIONS AND METHODS OF ENHANCING TRANSDERMAL AND TRANSMEMBRANE PENETRATION SYSTEMIC AGENTS

This invention relates to compositions and a method for the transdermal and transmembrane drug delivery of topical and physiologically active agents. More specifically, this invention relates to improved compositions for topical application and a method for enhancing the transdermal and transmembrane penetration of pharmacologically active substances using certain amides of heterocyclic amines as enhancing agents.

These amides are known compounds and have been reported for use as insect repellants (*J. Georgia Entomol. Soc.*, 14 (2), April, 1979, 166–174.

Since the skin is the largest and most accessible tissue for drug delivery, transdermal delivery systems are finding more applications for the administration of pharmacologically active substances. Due to this potential usefulness of skin as a route of drug administration for systemic therapy, the technology in this area is rapidly advancing.

Many attempts to enhance the penetration of pharmacologically active substances both locally and through the skin have been made. The more popular approach has been the employment of surface active agents. However, many surface active agents enhance the permeability by actually damaging the barrier tissue. Only slight to moderate enhancement of penetration is effected with the prior art surface active agents.

Another well known method for enhancing the penetration of active substances is the use of certain organic solvents such as, for example, dimethylsulfoxide and similar sulfoxides, dimethylacetamide and pyrrolidone. A disadvantage of using these solvents is that they are systemically distributed in a short period of time and cause undesirable side effects.

U.S. Pat. No. 4,316,893 discloses the employment of 1-substituted-azacycloheptan-2-ones, such as, for example, 1-dodecylazacycloheptan-2-one(azone) as enhancing agents.

An effective transdermal route of drug delivery can provide many advantages over the oral route. Side effects associated with the oral route of administration could be diminished or overcome. For example, a first pass metabolism can be avoided, i.e., reduction of metabolism due to an initial bypass of the liver. The transdermal route of entry could provide the ability to control the administration of drugs that have a small therapeutic index, i.e., drugs that have a narrow range between their therapeutic and toxic levels. A further advantage is that the transdermal route avoids the gastrointestinal tract and the side effects arising from gastrointestinal disturbances. A still further advantage would be the targeting of the site, i.e., delivering the drug directly into the systemic circulation.

Because of the above listed potential advantages of transdermal drug delivery, researchers have long sought an effective means of introducing drugs into the systemic circulation by applying them to the unbroken skin. However, the skin presents a formidable barrier to drug penetration. These barrier properties reside principally in the stratum corneum, the outermost layer composed of close packed dead keratinized cells. The penetration of the substances applied to the skin surface is inversely related to the thickness of the stratum corneum layer.

The topical route of administration was intended solely for localized action and because of the above noted skin barrier this route only rarely has been employed to obtain a systemic effect. Indeed, many problems have also been encountered when attempting to treat localized conditions. Some medicaments are not well absorbed and therefore require higher doses.

It is therefore an object of this invention to provide improved compositions for topical application and provide a method of enhancing transdermal and transmembrane penetration of pharmacologically active substances without adverse side effects, systemically or locally, on the skin or body membranes.

It is also a further object to provide improved compositions for localized action for agents that are not well absorbed and therefore are not too effective locally.

These and other objects are attained by the use of compositions and a method as described in more detail below.

The compositions of this invention contain a safe and effective amount of a pharmacologically active substance and from about 0.1 percent to about 100 percent of an amide of heterocyclic amines as a penetration enhancer in a nontoxic pharmaceutical vehicle. The amide enhancer has the following structural formula:

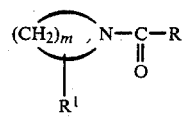

Formula 1 where:
m is 4–9;
$R^1$ is hydrogen or an alkyl group having from 1 to 8 carbon atoms; and
R is a straight or branched chain alkyl group having from 1 to 20 carbon atoms.

Particular compounds of Formula 1 are those in which m is 4–6, $R^1$ is hydrogen, and R is a straight or branched chain alkyl group having from 1 to 20 carbon atoms.

In particular the compound of Formula 1 is that in which m is 6, $R^1$ is hydrogen, and R is undecyl, the compound being hexamethylenelauramide.

The above composition is compatible with epidermal chemistry and enables ready transfer of the pharmacologically active substance from the vehicle to the skin. More important, the above composition enhances the penetration of active substance through the intact skin and delivers the substance to the systemic circulation at a constant and controlled rate.

By the term pharmacologically active substance used herein is meant a broad class of chemical and therapeutic agents which are sufficiently potent such that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, antiinflammatory agents, antimigraine preparations, antimotion sickness, antinauseants, antineoplastics, antiparkinsonism drugs, antipruritics, antipsychotics, antipyretics, antispasmodics, including gastrointestinal and urinary, anticholionergics, sympathomimetics, xanthine derivatives, cardiovascular preparations including calcium channel blockers, beta-blockers, antiarrythmics, antihypertensives, diuretics, vasodilators incuding general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

The compositions in accordance with this invention can be formulated in a variety of dosage forms for topical application. A wide variety of dermatologically acceptable inert carrier well known to the art may be employed. The topical compositions may include liquids, creams, lotions, ointments, gels, sprays, aerosols, skin patches, and the like. Typical inert carriers could be, for example, water, ethyl alcohol, polyvinyl pyrrolidone, propylene glycol, mineral oil, stearyl alcohol, spermaciti and gel-producing substances.

All of the above dosage forms and carriers are well known to the cosmetic and pharmaceutical art. The choice of the dosage form is not critical to the efficacy of the amide penetrating enhancer or the pharmacologically active substance.

The amides of Formula 1 were tested to determine the percent diffusion of various substances through hairless mouse skin into saline (pH 7.4) at 25° C. for 24 hours in the presence of B 5% of different enhancers in 20% propylene glycol and ethanol. (*Franz, T. J., Journal of Investigative Dermatology*, 64, 190 (1975)). They were compared to other well known enhancing agents. Results of this test are set forth in Table 1.

TABLE 1[a]

| Enhancing Agent | Hydro-cortisone 1% | Griseo-fulvin 1% | Erythro-mycin 2% |
|---|---|---|---|
| $CH_2(CH_2)_4CH_2NCO(CH_2)_6CH_3$ | 46 ± 8 | 6 ± 2 | 21 ± 10 |
| $CH_2(CH_2)_4CH_2NCO(CH_2)_{10}CH_3$ | 67 ± 6 | 31 ± 17 | 20 ± 10 |
| $CH_2(CH_2)_4CH_2NCO(CH_2)_{14}CH_3$ | 70 ± 8 | 14 ± 7 | 22 ± 12 |
| $CH_2(CH_2)_3CH_2NCO(CH_2)_6CH_3$ | 41 ± 17 | 17[b] | 19 ± 7 |
| $CH_2(CH_2)_3CH_2NCO(CH_2)_{10}CH_3$ | 67 ± 7 | 33 ± 15 | 18 ± 5 |
| $CH_2(CH_2)_3CH_2NCO(CH_2)_{14}CH_3$ | 64 ± 10 | 33[b] | 23 ± 7 |
| $CH_2(CH_2)_2CH_2NCO(CH_2)_6CH_3$ | 15 ± 2 | | 2 ± 1 |
| $CH_2(CH_2)_2CH_2NCO(CH_2)_{10}CH_3$ | 83 ± 11 | 26 ± 5 | 18 ± 3 |
| $CH_2(CH_2)_2CH_2NCO(CH_2)_{14}CH_3$ | 60 ± 9 | | 35 ± 10 |
| Azone | 64 ± 6 | 36 ± 19 | 24 ± 10 |
| Decyl Methyl Sulfoxide | 16 ± 6 | 8 ± 1 | 4 ± 1 |

TABLE 1[a-continued]

| Enhancing Agent | Hydro-cortisone 1% | Griseo-fulvin 1% | Erythro-mycin 2% |
|---|---|---|---|
| None | 1.4 ± 1 | <1 | 1.6 ± 0.5 |

[a] 5 to 12 skins in at least two independent experiments each time with fresh solution.
[b] 2 skins in one experiment.

The results clearly indicate that the amide compounds of Formula 1 enhance the penetration of hydrocortisone, griseofulvin and erythromycin through mouse skin. The results further indicate that the enhancing power of certain compounds is equivalent to, or greater than that of (1-n-dodecylazacycloheptan-2-one) (Azone), an agent currently employed as a penetration enhancer (U.S. Pat. No. 3,989,816). The results further indicate that decyl methyl sulfoxide (U.S. Pat. No. 3,678,156) was only about one fourth as active as the compounds of Formula 1. When the vehicle alone was tested, there was no enhancement of penetration of the ingredients through the mouse skin.

A particular compound of this invention, hexamethylenelauramide, was also tested as a penetration enhancer in the eye. The apparent corneal permeability of a water soluble compound such as Guanethidine was greatly enhanced (30 fold).

The penetration enhancers of Formula 1 can be prepared by any conventional method yielding amides. The enhancers described in this invention were prepared by acylation of the cyclic amines with long-chain acid halides. Preferably this is accomplished in a two phase system of chloroform and aqueous potassium carbonate.

The penetration enhancers disclosed herein may be used in combination with the pharmacologically active substance or may be used separately as a pre-treatment of the skin or other body membrane through which the active substance is intended to be delivered.

The following examples are not limiting but merely illustrative of this invention:

EXAMPLE 1

Hexamethylenelauramide

To a solution of 19.8 g. hexamethyleneimine (0.2 mol) in 200 ml. of chloroform, 100 ml. of water, and 20 g. of potassium carbonate was added 43.75 g. of lauroyl chloride in 100 ml. of chloroform in a dropwise fashion with vigorous stirring at room temperature over a 1–2 hour period. Upon completion, the mixture was stirred at room temperature for one hour. The organic phase was separated, washed with water, dried over magnesium sulfate, and concentrated. The residue was distilled at 153°–158° C./0.001 mm Hg to yield hexamethylenelauramide.

The structure was confirmed by $^{13}C$ NMR and IR spectroscopy and the purity (98.5%) was determined by GLPC analysis (3% OV-101 on Gas Chrom Q).

EXAMPLE 2

Substituting acetyl chloride, octanoyl chloride and palmitoyl chloride as starting materials for lauroyl chloride and following the procedure of Example 1, gives the following products respectively:

Hexamethyleneacetamide
Hexamethyleneoctamide
Hexamethylenepalmitamide

EXAMPLE 3

Substituting piperidine and pyrrolidine as starting materials for hexamethyleneimine and following the procedure of Example 1 yields the following respective products:

Piperidinelauramide
Pyrrolidinelauramide

EXAMPLE 4-SOLUTION

| Ingredients | Percent W/W |
| --- | --- |
| Hydrocortisone | 1 |
| Hexamethylenepalmitamide | 5 |
| Propylene Glycol | 15 |
| Ethanol q.s. | 100 |

EXAMPLE 5-CREAM

| Ingredients | Percent |
| --- | --- |
| Griseofulvin | 2.0 |
| Pyrrolidinelauramide | 20.0 |
| Triethanolamine | 0.06 |
| Glycerin | 2.5 |
| Glyceryl Monostearate | 3.5 |
| Stearic Acid | 12.0 |
| Water, q.s. | 100.0 |

EXAMPLE 6-OINTMENT

| Ingredients | Percent W/W |
| --- | --- |
| Erythromycin | 1.5 |
| Piperidinelauramide | 15.0 |
| Polyethylene Glycol Ointment to | 100.0 |

EXAMPLE 7-OINTMENT

| Ingredients | Percent W/W |
| --- | --- |
| Polyethylene Glycol 4000 | 33.0 |
| Cetyl Alcohol | 5.0 |
| Polysorbate 60 | 5.0 |
| Isopropyl Myristate | 5.0 |
| Propylene Glycol | 10.0 |
| Polyethylene Glycol 300 | 21.0 |
| Cimetidine base | 1.0 |
| Hexamethylenelauramide | 20.0 |

EXAMPLE 8-GEL

| Ingredients | Percent W/W |
| --- | --- |
| Hydrocortisone | 1.0 |
| Hexamethylenelauramide | 5.0 |
| Propylene Glycol | 10.0 |
| Isopropyl Myristate | 10.0 |
| Carbomer 940 | 3.5 |
| Citric Acid, Monohydrate | 0.1 |
| Alcohol q.s. | 100.0 |

EXAMPLE 9-CREAM

| Ingredients | Percent |
| --- | --- |
| Trifluorothymidine | 1.0 |
| Hexamethylenelauramide | 10.0 |
| Emulsifying Wax | 15.0 |
| Light Mineral Oil | 5.0 |
| Benzyl Alcohol | 0.5 |
| Imidazolidinyl Urea | 0.3 |
| Purified Water q.s. | 100.0 |

EXAMPLE 10-LOTION

| Ingredients | Percent |
| --- | --- |
| Trifluorothymidine | 2.0 |
| Hexamethylenelauramide | 1.0 |
| Imidazolidinyl Urea | 0.3 |
| Benzyl Alcohol | 0.5 |
| PEG-24 Hydrogenated Lanolin | 1.0 |
| Purified Water q.s. | 100.0 |

The above solutions, lotion, ointments, creams and gel were all prepared according to methods well known to the pharmaceutical art.

What is claimed is:

1. A topical composition for enhancing the transdermal and transmembrane penetration of pharmacologically active substances which are systemically active in the blood stream which comprises an effective amount of said substance and from about 0.1 to 100% of a compound having the structural formula:

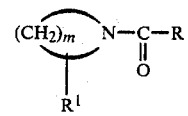

in which:
  m is 4 to 9;
  $R^1$ is hydrogen or an alkyl group having from 1 to 8 carbon atoms; and
  R is a straight or branched chain alkyl group having from 1 to 20 carbon atoms.

2. The composition of claim 1 in which the active substance is an antibiotic.

3. The compound of claim 2 in which m is 4 to 6, $R^1$ is hydrogen, and R is from 1 to 20.

4. The composition of claim 3 in which m is 6, $R^1$ is hydrogen, and R is undecyl, the compound being hexamethylenelauramide.

5. The composition of claim 2 in which the antibiotic is selected from the group consisting of erythromycin and lincomycin.

6. The composition of claim 1 in which the active substance is an antifungal agent.

7. The composition of claim 1 in which the active substance is a steroid.

8. A method for enhancing the transdermal and transmembrane penetrations of pharmacologically active systemic substances into the blood stream which comprises topically administering to a human or animal a composition comprising an effective amount of said active substance and a penetrating amount of a compound having the formula:

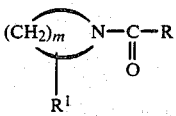

in which:

m is 4 to 9;

$R^1$ is hydrogen or an alkyl group having from 1 to 8 carbon atoms; and

R is a straight or branched chain alkyl group having from 1 to 20 carbon atoms.

9. The method of claim 8 in which the active substance is an antibiotic.

10. The method of claim 8 in which the active substance is an antifungal agent.

11. The method of claim 8 in which the active substance is a steroid.

12. The method of claim 8 in which m is 6 and $R^1$ is undecyl, being the compound hexamethylenelauramide.

* * * * *